United States Patent
Hoben et al.

(10) Patent No.: US 6,740,076 B2
(45) Date of Patent: May 25, 2004

(54) ULTRASONIC SEPTUM MONITORING FOR IMPLANTABLE MEDICAL DEVICES

(75) Inventors: Richard Hoben, Lanaken (BE); Adrianus Donders, Faunex (CH)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 10/132,320

(22) Filed: Apr. 26, 2002

(65) Prior Publication Data
US 2003/0204165 A1 Oct. 30, 2003

(51) Int. Cl.[7] .................................................. A61K 9/22
(52) U.S. Cl. ............................. 604/891.1; 604/93.01
(58) Field of Search .................... 600/461; 128/899, 128/DIG. 12, DIG. 13; 604/67, 93.01, 132, 153, 212, 245–246, 403, 404, 407, 890.1, 891.1, 892.1

(56) References Cited

U.S. PATENT DOCUMENTS

| | | | |
|---|---|---|---|
| 4,573,994 A | * | 3/1986 | Fischell et al. .......... 604/891.1 |
| 4,760,837 A | | 8/1988 | Petit ....................... 604/891.1 |
| 4,804,054 A | | 2/1989 | Howson et al. .............. 128/898 |
| 5,006,115 A | | 4/1991 | McDonald .................. 604/175 |
| 5,009,644 A | | 4/1991 | McDonald .................. 604/175 |
| 5,171,228 A | | 12/1992 | McDonald .................. 604/175 |
| 5,201,715 A | * | 4/1993 | Masters ..................... 604/175 |
| 5,957,890 A | * | 9/1999 | Mann et al. ................. 604/131 |
| 6,009,878 A | | 1/2000 | Wijand et al. .............. 128/899 |
| 6,287,293 B1 | * | 9/2001 | Jones et al. .............. 604/891.1 |
| 6,305,381 B1 | | 10/2001 | Wijand et al. .............. 128/898 |

* cited by examiner

Primary Examiner—Francis J. Jaworski
(74) Attorney, Agent, or Firm—Girma Wolde-Michael; Daniel G. Chapik (57) ABSTRACT

Methods and systems for monitoring the condition of a septum in an implantable medical device are disclosed. Monitoring of the septum provides the ability to determine whether a needle has pierced the septum to effect the transfer of fluids into or out of a reservoir in the implantable medical device. Septum monitoring may provide the ability to determine whether the septum is maintaining its ability to seal the reservoir against leakage. The systems of the present invention include an ultrasonic transducer acoustically coupled to the septum to emit ultrasonic energy directly into the septum. Insertion of a needle through the septum can be detected by the acoustical changes caused by the needle located within the septum.

61 Claims, 8 Drawing Sheets

ULTRASONIC SEPTUM MONITORING FOR IMPLANTABLE MEDICAL DEVICES

FIELD OF THE INVENTION

The present invention relates to the field of implantable medical devices. More particularly, the present invention relates to systems and methods for monitoring septums in implantable medical devices.

BACKGROUND

Many implantable medical devices require percutaneous communication with devices external to the body in which the implantable medical device is located. For example, implantable medical devices that dispense drugs within the body may require periodic replenishment of the drug located in a reservoir of the device. Typically, such replenishment is accomplished by advancing a needle (or similar device) through the skin into a reservoir of the device and transferring fluids through the needle.

Because the device is implanted within the patient and cannot be seen directly, care must be taken to ensure that the needle is properly placed into the device before transferring fluids. If the needle is not located within the reservoir, delivery of the drug through the needle can result in immediate delivery of a significant quantity of the drug to the patient, with potentially dire consequences. In addition, failure to properly refill the reservoir may also have potentially dire consequences for the patient when the needed medication is not dispensed at a later time.

Attempts to address the problem of needle location within a septum have taken two general approaches. In one set of approaches, the location of the septum is determined by various techniques including antennas located on the surface of the patient. One potential issue with this approach is that even after location of the septum is accurately determined, perforation of the septum by the needle may not necessarily be guaranteed during fluid transfer.

Another set of approaches involves determining whether the needle is located within the reservoir after it has been advanced. One variation of this approach involves closing an electronic circuit to provide an indication that the needle is in physical contact with a selected location within the reservoir. Another variation involves providing tactile and/or audible feedback to the operator of the needle when the needle causes deflection of a resilient portion of the reservoir. Another approach to determine whether a needle has pierced a septum in an implantable medical device involves sensing the location of needle within the reservoir by detecting a change in impedance of an air inductor or an eddy current detector within the reservoir of the device.

Still another approach involves the use of a multi-layered septum including conductive layers. When a needle pierces the septum, electrical connection between the conductive layers through the needle piercing the layers provides an indication that the septum has been pierced. One issue with this approach is that one of the conductive layers may need to be exposed within the reservoir, which may not be desirable if the conductive materials are not compatible with the drugs or other materials located within the reservoir.

Another issue with many of these approaches is that the needle itself must be electrically conductive. As a result, more recent advancements in the use of polymeric needles may be incompatible with many of these approaches because polymeric needles will typically be electrically nonconductive.

Examples of these approaches may be described in one or more of the patents listed in the following Table I.

TABLE I

| U.S. Pat. No. | Inventor | Issue Date |
| --- | --- | --- |
| 4,760,837 | Petit | Aug. 2, 1988 |
| 4,804,054 | Howson et al. | Feb. 14, 1989 |
| 5,006,115 | McDonald | Apr. 9, 1991 |
| 5,009,644 | McDonald | Apr. 23, 1991 |
| 5,171,228 | McDonald | Dec. 15, 1992 |
| 6,009,878 | Weijand et al. | Jan. 4, 2000 |
| 6,305,381 B1 | Weijand et al. | Oct. 23, 2001 |

All references listed in Table I, and elsewhere herein, are incorporated by reference in their respective entireties. As those of ordinary skill in the art will appreciate readily upon reading the Summary of the Invention, Detailed Description of the Preferred Embodiments, and claims set forth below, at least some of the devices and methods disclosed in the references of Table I and elsewhere herein may be modified advantageously by using the teachings of the present invention. However, the listing of any such references in Table I, or elsewhere herein, is by no means an indication that such references are prior art to the present invention.

SUMMARY OF THE INVENTION

The present invention has certain objects. That is, various embodiments of the present invention provide solutions to one or more problems existing in the prior art with respect to septums located in implantable medical devices. One such problem is that, in some situations, it is difficult or impossible to determine whether a needle meant to pierce a septum is, in fact, present in the septum. As a result, drugs may not be properly delivered to the reservoirs of implantable medical devices through septums in those devices. As noted above, in some situations the drug may be dispensed directly to the patient with potentially dire consequences. In other situations, the drug is not available in the reservoir of the implantable medical device for dispensing when needed at a later time.

In comparison, the systems and methods of the present invention can be used to monitor the condition of a septum in an implantable medical device. Monitoring of the septum provides the ability to determine whether a needle has pierced the septum to effect the transfer of fluids into or out of a reservoir in the implantable medical device. Alternatively, monitoring of the septum may provide the ability to determine whether the septum is maintaining its ability to seal the reservoir against leakage.

The systems of the present invention include an ultrasonic transducer mounted to direct ultrasonic energy into the septum. The ultrasonic transducer is preferably directly acoustically coupled to the septum. Insertion of a needle into the septum can be detected by the acoustical changes caused by the needle located within the septum. The ultrasonic transducer can be operated in either pulse mode or impedance mode. In pulse mode, a short electrical pulse is used to drive the ultrasonic transducer. The ultrasonic transducer converts the electrical energy into acoustic energy traveling through the septum.

In the absence of a needle, the ultrasonic energy will typically be reflected by the opposing side of the opening in which the septum is located. Insertion of a needle into the septum will, however, result in an early reflection of the ultrasonic energy directly from the needle, and/or a change in the pattern of reflected ultrasonic energy within the opening. Such changes in reflection of the ultrasonic energy can be used to provide an indication that the septum has been pierced by a needle.

If the ultrasonic transducer is operated in impedance mode, the transducer is driven (by, for example, a swept sine wave) while measuring its response. The response of the ultrasonic transducer is indicative of the acoustic load on the ultrasonic transducer for each applied frequency. That acoustic load will be changed by the insertion of a needle into the septum, degradation of the septum, leakage around the septum, etc.

Whether the ultrasonic transducer is driven in pulse mode or impedance mode, it may be desirable to compare measurements obtained at different times to determine whether a needle is present within the septum. Typically, such comparisons will be made based on a reference signal identified shortly before advancement of the needle, followed by signals obtained after advancement of the needle by an operator.

The decision to obtain a reference signal can be invoked by telemetric communication with the implantable medical device to provide an indication that a transfer procedure is about to occur. At that point, a reference signal can be obtained using the ultrasonic transducer before the needle is inserted through the skin of the patient. From that point in time, repeated measurement cycles may be performed until detection of the needle piercing the septum occurs.

Another advantage of the systems and methods of the present invention is their compatibility with polymeric needles that are typically electrically nonconductive. Many of the previous approaches to sensing needle presence in a septum have relied on electrically conductive needles that are typically metallic. The systems and methods of the present invention are, however, capable of detecting any needle that presents a hard, acoustically reflective surface, regardless of the electrical conductivity of the material or materials used to construct the needle.

An additional advantage of the present invention is that further measurements with the ultrasonic transducer may be obtained after removal of the needle from the septum. Such measurements may be used to provide an indication regarding the condition of the septum after removal of the needle. One use for such a measurement is to determine whether the condition of the septum is such that leakage may be occurring through or around the septum.

These and other objects, advantages, and features of the invention may be understood more completely with reference to the following detailed description of specific embodiments of the invention.

DETAILED DESCRIPTION OF THE PREFERRED EMBODIMENTS

Figure 1:
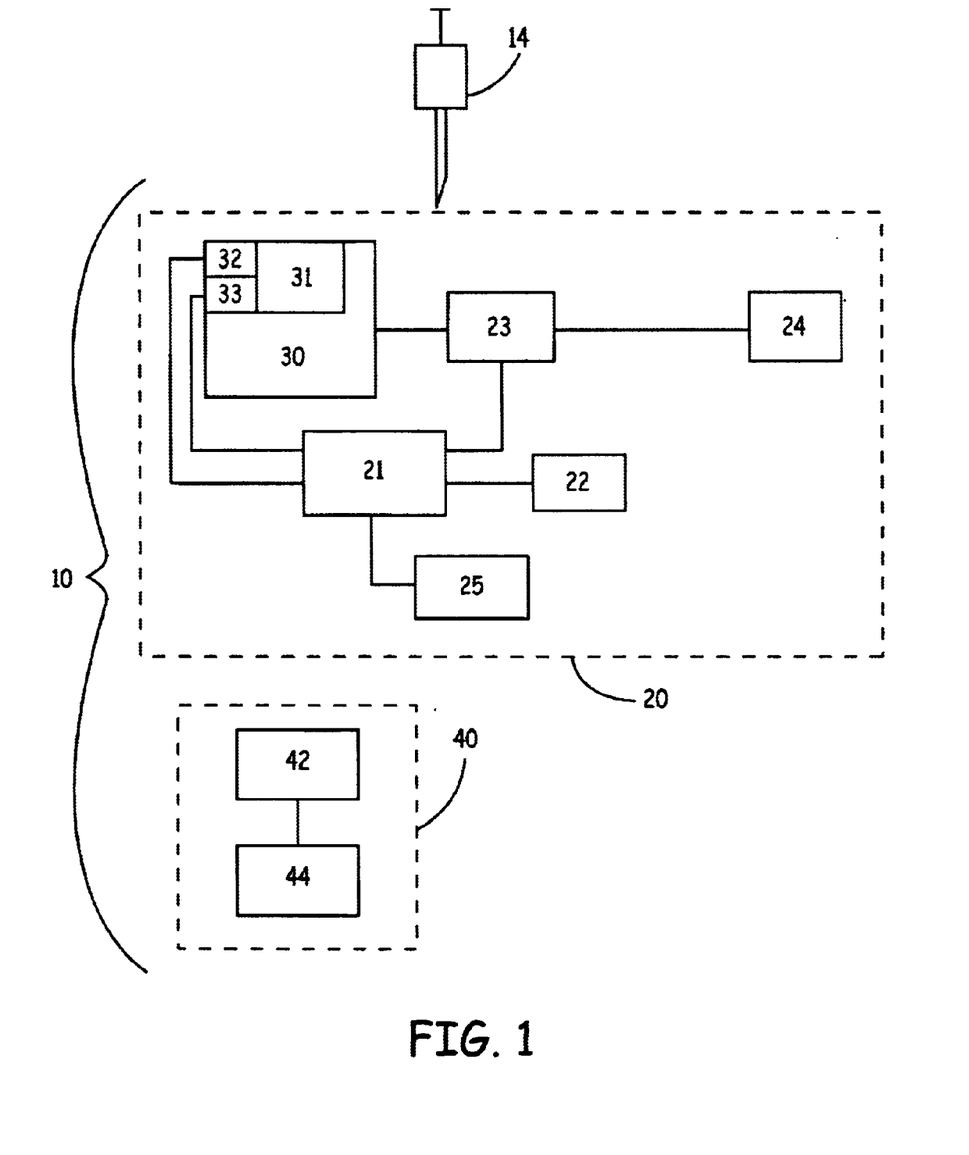
FIG. 1 is a block diagram depicting one system according to the present invention.

FIG. 1 is a block diagram depicting one system 10 according to the present invention. The system 10 includes an implantable medical device 20 located beneath the skin 12 of a patient. Also depicted in FIG. 1 is a syringe 14 including a needle that may be used to pierce the septum in the implantable medical device 20 as will be discussed in more detail below.

The device 20 may be of any suitable design, such as a SYNCHROMED Implantable Drug Pump available from Medtronic, Inc., although other implantable medical devices may be used in connection with the present invention. The depicted implantable medical device 20 may include a variety of components including a controller 21 and a power supply 22 (which may preferably be in the form of a battery or other self-contained power source). The controller 21 may preferably be in the form of a digital microprocessor, although any equivalent device may be substituted for a digital microprocessor. In many instances, it may also be desirable that the controller 21 include data storage capabilities.

Also associated with the implantable medical device is a pump 23 used to deliver a drug or other fluid from the implantable medical device 20 to the patient through an outlet catheter 24. The device 20 further includes a reservoir 30 that contains a supply of the drug to be delivered by the pump 23 through the catheter 24.

Although not depicted, the device 20 may also include components such as safety valves, flow restrictors, etc. that may enhance operation of the implantable medical device. Examples of such components may be described in, for example, U.S. Pat. Nos. 6,203,523 and 6,048,328, both to Haller et al.

The reservoir 30 of the implantable medical device 20 includes a septum 31 that seals an opening into the reservoir 30. The septum 31 may be manufactured of any suitable material or materials. Typically, the septum 31 will include elastomeric materials, for example, silicone rubber, that are piercable by a needle of a syringe 14 (which itself does not necessarily form a part of the system 10) and compatible with the drugs to be contained within the reservoir 30.

A detector 33 is also depicted in FIG. 1 in connection with the septum 31 and ultrasonic transducer 32. The detector 33 is arranged to detect ultrasonic energy emitted by the ultrasonic transducer 32 after the ultrasonic energy has passed through at least a portion of the septum 31. It may be preferred that the detector 33 be arranged relative to the septum 31 and the ultrasonic transducer 32 such that it detects ultrasonic energy only after the ultrasonic energy has passed through substantially all of the septum 31.

Although the detector 33 is depicted in FIG. 1 as a separate component in addition to the ultrasonic transducer 32, it will be understood that in some instances, the detector 33 and the ultrasonic transducer 32 will be the same physical component, for example, a piezoelectric ultrasonic transducer or similar structure capable of converting electrical energy to ultrasonic energy as well as the opposite, that is, converting ultrasonic energy to electrical energy.

Both the ultrasonic transducer 32 and the detector 33 are connected to the controller 21 which supplies electrical energy and control signals that cause the ultrasonic transducer 32 to emit ultrasonic energy. In addition, the controller 21 is capable of receiving signals from the detector 33 that are indicative of the ultrasonic energy detected by the detector 33. In one alternative, the ultrasonic transducer 32 may be connected directly to the power source 22, with the controller 21 providing control signals to the ultrasonic transducer 32 for operation.

The implantable medical device 20 also preferably includes a telemetry assembly 25 that is capable of providing two-way communication between the implantable medical device 20 and any suitable external indicator unit 40. Communication between the telemetry assembly 25 and the external indicator unit 40 may be accomplished using any suitable technique, for example, RF transmission, infrared, ultrasonics, etc.

The external indicator unit 40 preferably includes a telemetry assembly 42 capable of communicating with the telemetry assembly 25 included in the implantable medical device 20. The external indicator unit 40 may also preferably include a condition indicator 44 to communicate the condition of the septum 31 to an operator. The condition indicator 44 may be self-contained, that is, the condition indicator 44 itself may provide a visual, audible, tactile, or other indicator to an operator. Alternatively, the condition indicator 44 may provide, for example, a signal to another unit regarding the condition of the septum 31 in the implantable medical device 20. For example, the condition indicator 44 may provide a signal to a computerized control device outside of the external indicator unit 40.

Figure 2:
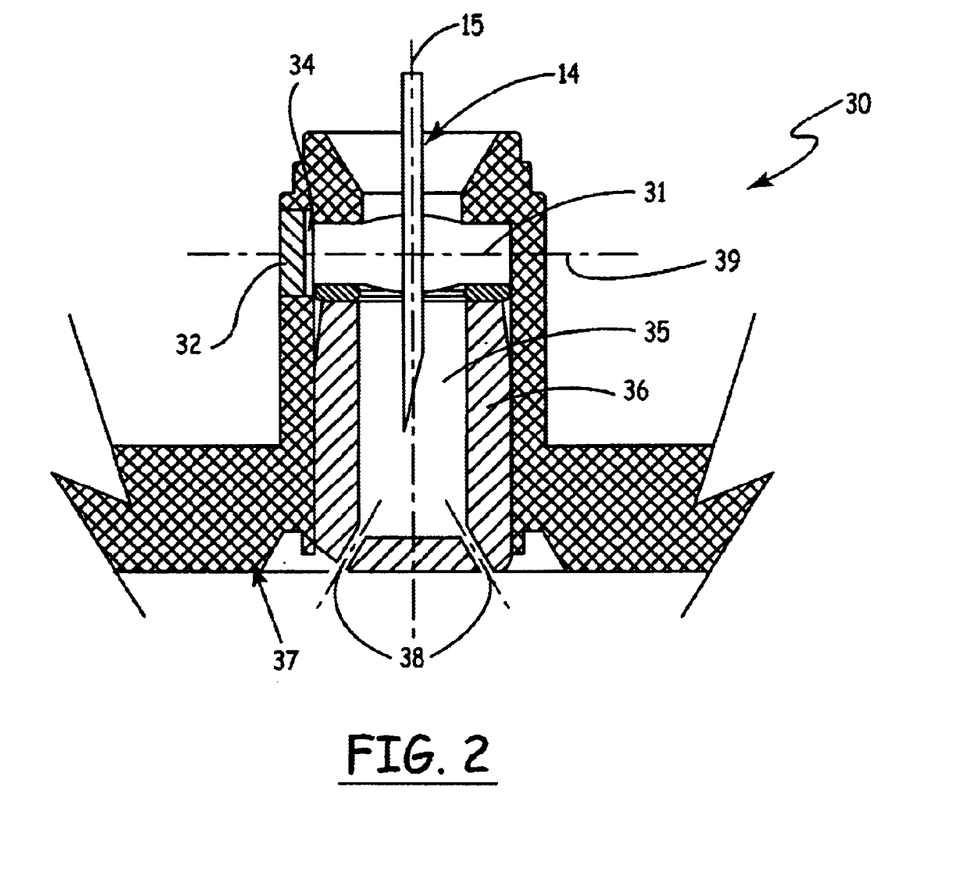
FIG. 2 is a cross-sectional view of a portion of one reservoir in an implantable medical device that includes a septum sealing an opening therein.

FIG. 2 is a cross-sectional view of one embodiment of a reservoir 30 and septum 31 that may be used in connection with the implantable medical device 20 of FIG. 1. The reservoir 30 includes a housing 37 that contains a septum plug 36 used to retain the septum 31 while providing a fluid-tight seal. The septum plug 36 preferably defines a septum chamber 35 including drain holes 38 that allow fluids delivered to the septum chamber 35 to pass into the remainder of the reservoir in the implantable medical device 20.

The septum 31 and the opening in which it is located preferably define an insertion axis 15. The insertion axis 15 is the preferred or principal axis along which a needle 14 is advanced during piercing of the septum 31. In most instances, the insertion axis 15 will be normal to the plane in which the septum 31 and its associated opening are located. It will be understood that variations in the exact path of the needle 14 may be possible provided that the needle 14 pierces the septum 31 in a manner that results in its distal end being located in position to transfer fluids safely to the reservoir.

FIG. 2 also depicts an ultrasonic transducer 32 arranged to direct ultrasonic energy into the septum 31. The ultrasonic transducer 32 is preferably arranged to direct its energy along a principal axis 39 that is transverse to the insertion axis 15. By transverse, it is meant that the principal axis 39 (and the ultrasonic energy emitted by the ultrasonic transducer 32 along that axis) crosses the insertion axis 15 at an angle greater than zero degrees. More preferably, the principal axis 39 crosses the insertion axis 15 at an angle greater than 45 degrees or more. And more preferably, the principal axis 39 crosses the insertion axis 15 at an angle of 90 degrees as depicted in, for example, FIG. 2.

Among the considerations in selecting an ultrasonic transducer 32 to use in connection with the present invention is the need to provide coverage over the entire opening in which the septum 31 is located such that insertion of a needle in any portion of the septum 31 can be detected. For example, it may be desirable to use an ultrasonic transducer 32 that has a divergence angle sufficiently large to direct ultrasonic energy throughout the septum 31. One technique that may be used to increase divergence angle of an ultrasonic transducer 32 is to reduce the radiating surface of the ultrasonic transducer 32 such that, for example, the transducer 32 approximates a point source from which a widely diverging waveform is emitted.

Another manner in which the location and orientation of the ultrasonic transducer 32 can be characterized is in terms of the septum 31 and the opening in which it is located. More particularly, the ultrasonic transducer 32 may be described as directing ultrasonic energy across the septum 31 and its opening. Alternatively, the ultrasonic transducer 32 can be described as directing ultrasonic energy from one side of the opening in which the septum 31 is located to the opposite side of the opening in which the septum 31 is located.

The opposing side of the opening in which the septum 31 is located may also function as a reflector of the ultrasonic energy emitted by the ultrasonic transducer 32. Although a separate reflector could be supplied, the surface of the opening will typically serve as a sufficient reflector of the ultrasonic energy emitted by the ultrasonic transducer 32.

In another variation, it may be desirable to use more than one ultrasonic transducer, with each ultrasonic transducer located in a different position about the periphery of the septum. For example, the ultrasonic transducers may be located directly opposite each other. In another example, the ultrasonic transducers may be located about the periphery of the septum such that they are separated by, for example, a 90 degree arc.

In the depicted embodiment, the ultrasonic transducer 32 is attached or coupled directly to the septum 31 via a layer of silicone adhesive 34 that provides a fluid-tight seal as well as sufficient transfer of the ultrasonic energy emitted by the ultrasonic transducer 32 to the septum 31. The ultrasonic transducer 32 itself is not in actual physical contact because of the intervening adhesive 34. For the purposes of the present invention, however, the ultrasonic transducer 32 will be considered to be directly acoustically coupled to a septum 31 that is located in physical contact with the materials that are in direct contact with the transducer 32. It may be preferred that the materials between the transducer 32 and the septum not be fluids (gas and/or liquid) to enhance acoustic coupling between the septum 31 and the transducer 32. For example, it may be preferred that the materials located between the septum 31 and transducer 32 be solid materials capable of efficiently transmitting acoustic energy.

Figure 3:
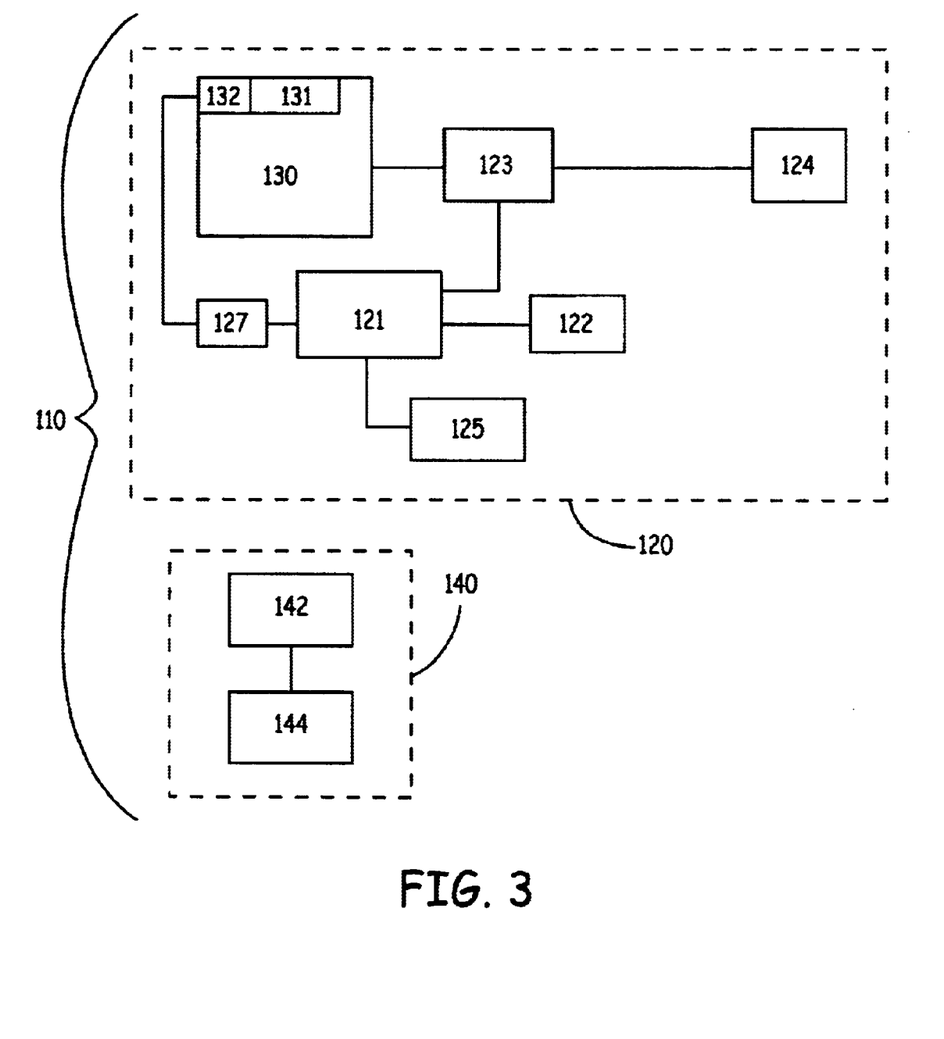
FIG. 3 is a block diagram depicting another system according to the present invention.

FIG. 3 depicts another system 110 according to the present invention. In many respects, the system 110 is similar to the system 10 of FIG. 1. For example, the system 110 includes an implantable medical device 120 that itself includes a controller 121, power source 122, pump 123, outlet catheter 124, and telemetry assembly 125. In addition, the implantable medical device 120 also includes a reservoir 130 sealed by a septum 131.

The system 110 also includes an external indicator unit 140 that includes a telemetry assembly 142 and a condition indicator 144 similar to the respective components in the system 10 of FIG. 1.

In addition, the system 110 also includes an ultrasonic transducer 132 arranged to direct ultrasonic energy into the septum 131. The system 110 does not, however, include a detector arranged to detect ultrasonic energy after it has passed through the septum 131. Rather, the system 110 includes a sensor 127 that is capable of sensing the acoustic load on which the ultrasonic transducer 132 operates when driven in impedance mode.

The ultrasonic transducer 132 may be driven in impedance mode using, for example, a swept sine wave, a square wave, etc., while measuring the response of the ultrasonic transducer 132 at various applied frequencies to determine the acoustic load on the ultrasonic transducer 132.

Although the load sensor 127 is depicted in FIG. 3 as a separate component in addition to the controller 121, it will be understood that in some instances, the sensor 127 and the controller 121 will be the same physical component, for example, a controller capable of sensing the acoustic load on the ultrasonic transducer 132 as it is driven by the applied driving signals.

It should be noted that a system may be designed for operation in either pulse or impedance mode. One system may be used in either mode when, for example, the ultrasonic transducer itself can perform the detection functions described above when used in pulse mode and the controller can monitor the load on the ultrasonic transducer when driven in impedance mode.

Figure 4:
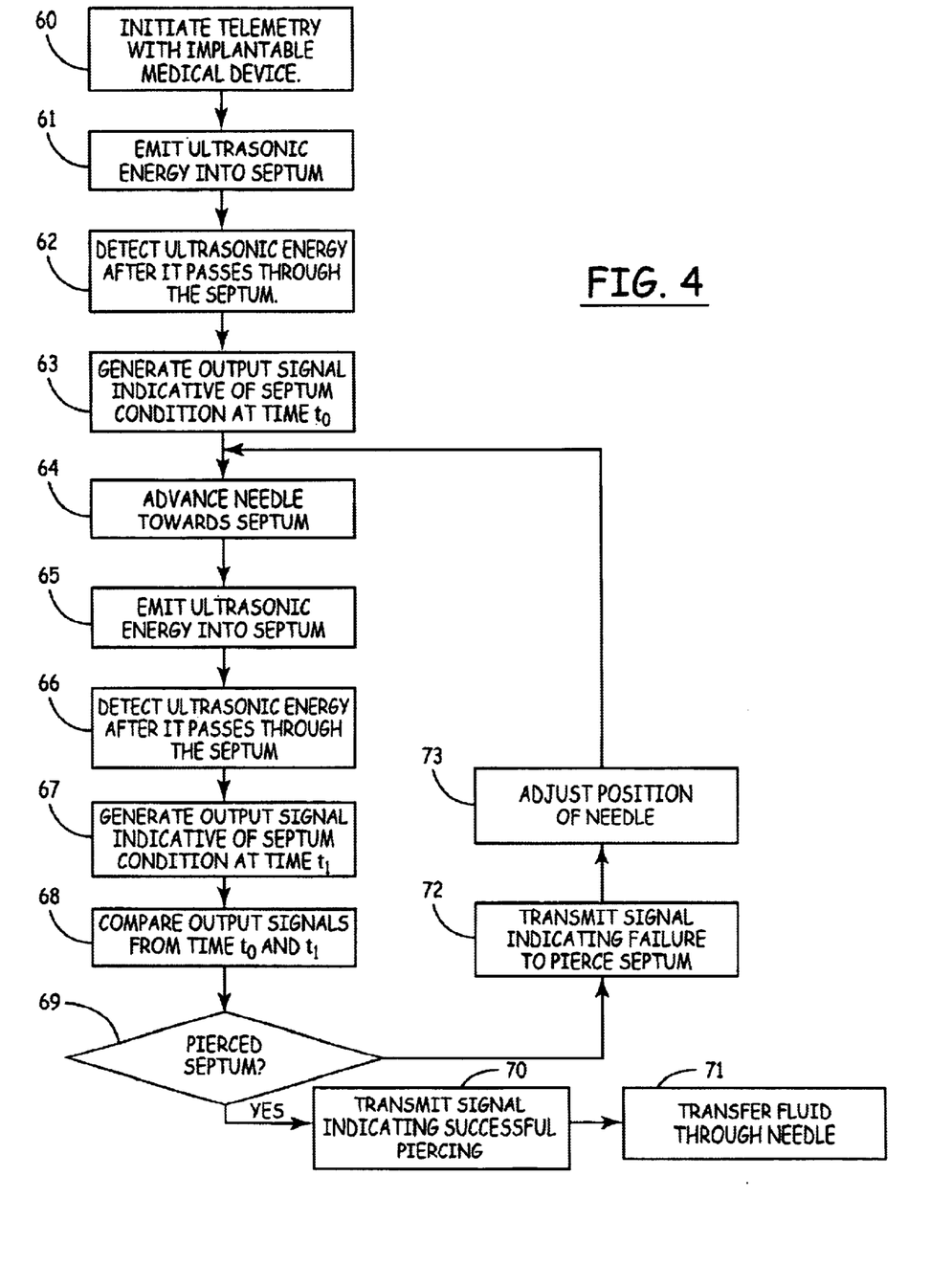
FIG. 4 is a flow chart of one method of monitoring a septum during advancement of a needle according to the present invention.

FIG. 4 is a flow diagram of operation of one system according to one method of the present invention. The method illustrated in FIG. 4 may be more suited for use in connection with the pulse mode of operating an ultrasonic transducer according to the present invention. Although not required, the method of the invention as depicted in FIG. 4 will typically began with initiation of telemetric communication with the implantable medical device 60. Although telemetric communication may be continuous between the implanted device and an external system, telemetric communication is more typically initiated at discrete intervals to conserve power within the implanted medical device.

After telemetric communication with the implantable medical device has been initiated, the device may be instructed or otherwise directed to emit 61 ultrasonic energy into a septum sealing a reservoir within the implanted medical device. After the ultrasonic transducer emits ultrasonic energy into the septum, the ultrasonic energy is detected 62 after it passes through at least a portion of the septum. In many instances, the ultrasonic energy will pass through substantially all of the septum. As discussed above in connection with the system 10 of FIG. 1, detection of the ultrasonic energy may be performed by a component distinct from the ultrasonic transducer used to emit the ultrasonic energy. Alternatively, the ultrasonic transducer used to emit ultrasonic energy may be used to detect that same energy after it has passed through at least a portion of the septum.

After detection of the ultrasonic energy, an output signal may be generated 63 by the detector that is indicative of the septum condition at a time $t_0$. The output signal may be generated by, for example, a controller associated with the implanted medical device (for example, controller 21 in system 10 of FIG. 1). Alternatively, the detector itself may generate a signal sufficient to serve as an output signal indicative of the condition of the septum.

After the output signal has been generated, the needle (or other fluid delivery device) is advanced 64 towards the reservoir and its associated septum. The exact position of the needle relative to the implanted medical device before advancement may be determined by a variety of the location and methods and systems described in the background section above. It is preferred that advancement of the needle be delayed until after the output signal has been generated for time $t_0$. By waiting to advance the needle until after the initial measurements have been taken, the system can obtain a baseline signal they can be used to determine whether the needle pierces the septum as it is advanced.

After initial advancement of the needle is completed or while advancement is occurring, the telemetry system preferably initiates a second round of ultrasonic energy emission 65 into the septum. After emission of the ultrasonic energy, detection 66 of the ultrasonic energy after it has passed through at least a portion of the septum is performed.

The detected ultrasonic energy is then used to generate an output signal 67 that is indicative of the septum condition at time $t_1$. This second round of ultrasonic energy detection will typically be performed in a manner similar to the detection used to generate the output signal indicative of the septum condition at time $t_0$.

With the output signals from times $t_0$ and $t_1$, a comparison can be performed 68 to determine whether the condition of the septum has changed between the two measurements based on the output signals generated at the different times. It should be noted that this comparison (and the data storage that may be required to complete it), may be performed within an implantable medical device itself or, alternatively, the comparison may be performed external to the patient based on the output signals which can be communicated by telemetry to an external control device. Regardless of the location of the controller used to perform the comparison functions, it will typically be preferred that the controller include at least some data storage capacity to provide for comparison of the output signals obtained at different times. Such data storage may be effected digitally or otherwise.

With the comparison complete, a decision is made as to whether the compared output signals indicate piercing of the septum by the needle 69. If the compared output signals indicate that the septum condition has changed in a manner that indicates piercing by the needle, then it may be desired that the implantable medical device transmit a signal 70 indicating successful piercing of the septum by the needle. Typically, that signal will be transmitted by the telemetry assembly associated with the implantable medical device. The telemetry assembly communicates with an external device that is capable of providing some indication to an operator by, for example, audible, visual, tactile, etc. techniques, that the septum has been successfully pierced by the needle.

Upon receipt of a signal indicating successful piercing of the septum, transfer of fluids through the needle may be commenced 71. That transfer may typically involve the delivery of a drug or drugs into the reservoir of the implantable medical device. Alternatively (or in addition) to delivery of fluids to the implantable medical device, the transfer may involve the removal of fluids from the reservoir of the implantable medical device through the needle.

If, however, the determination 69 as to whether the septum has been pierced based on the compared output signals is negative, that is, that the septum has not been pierced by the needle, then a signal is preferably sent to an external device that the needle has failed to pierce the septum 72. Typically, that signal will be transmitted by a telemetry assembly associated with the implantable medical device. The telemetry assembly communicates with an external device that is capable of providing some indication to an operator by, for example, audible, visual, tactile, etc. techniques, that the septum has not been pierced by the needle.

Upon receipt of the signal indicating a failure to pierce the septum, the position of the needle is preferably adjusted 73. The adjustments may include simply advancing the needle further inward along the same line of advancement toward the implantable medical device. Alternatively, the adjustment may involve withdrawal of the needle (partially or completely). In still another alternative, the adjustment may involve changing only the direction along which the needle is advanced.

In any case, the needle is again advanced towards the implantable medical device 64 as performed previously (before the indication of a failure to pierce the septum was received). Another round of ultrasonic energy emission 65 and detection 66 follows, with an output signal being generated 67. The new output signal is then compared 68 with the original output signal obtained at time $t_0$, followed by a determination as to whether the septum has been pierced 69. If the determination is positive, that is, the septum has been pierced, then a signal can be transmitted and relayed to the operator that a successful piercing has occurred 70. If the determination is negative, that is, that a successful piercing has not occurred, then an appropriate signal is relayed 72 and the needle position can again be adjusted 73 as discussed above.

Figure 5:
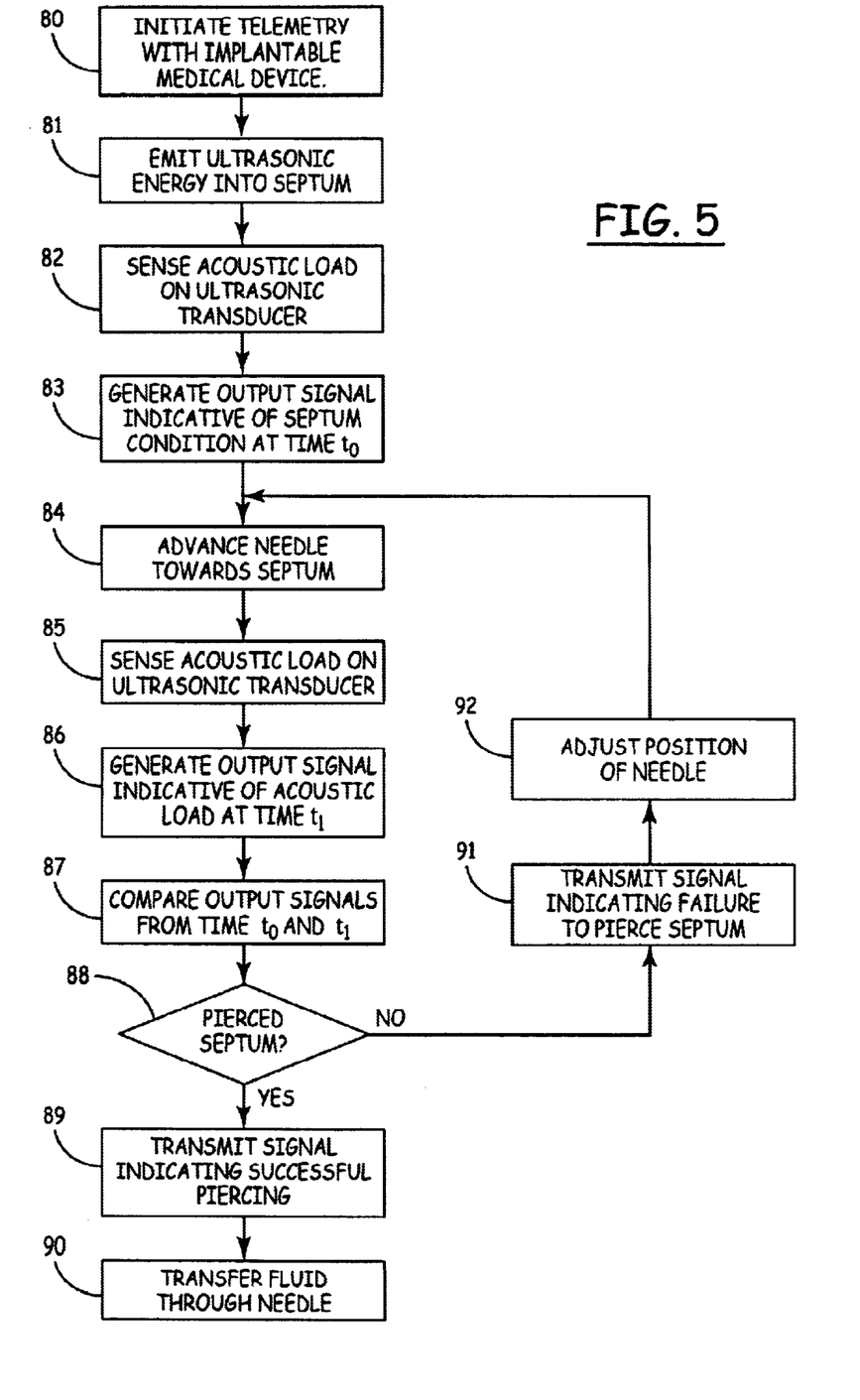
FIG. 5 is a flow chart of another method of monitoring a septum during advancement of the needle according to the present invention.

FIG. 5 is a flow diagram of operation of another system according to the present invention. The method illustrated in FIG. 5 may be more suited for use in connection with the impedance mode of operating an ultrasonic transducer according to the present invention. Although not required, the method of the invention as depicted in FIG. 5 will typically began with initiation of telemetry 80 with the implantable medical device. Although telemetric communication may be continuous between the implanted device and an external system, telemetric communication may more typically be performed at discrete intervals to conserve power within the implanted medical device.

After telemetry with the implanted medical device has been initiated, the implantable medical device may be instructed or otherwise directed to begin the emission of ultrasonic energy 81 into the septum sealing the reservoir within the implanted medical device. When operated in impedance mode, the emission of ultrasonic energy will typically be continuous while, for example, a swept sine wave driving signal is used to cause the ultrasonic transducer to emit ultrasonic energy. It should be understood, however, that the continuous nature of the emission may be periodic, that is, the emissions may be continuous for a period of time, followed by a period in which ultrasonic energy is not emitted by the ultrasonic transducer.

As the ultrasonic transducer emits ultrasonic energy into the septum, the acoustic load on the ultrasonic transducer is sensed 82 at various applied frequencies. As discussed above in connection with the system 110 of FIG. 3, sensing of the acoustic load may be performed by a component distinct from the controller, or by the controller itself.

After sensing the acoustic load on which the ultrasonic transducer is operating, an output signal may be generated 83 by the load sensor that is indicative of the septum condition at a time $t_0$. The output signal may be generated by, for example, a controller associated with the implanted medical device (for example, controller 121 in system 110 of FIG. 3). Alternatively, if a separate load sensor is used, the load sensor itself may generate a signal sufficient to serve as an output signal indicative of the acoustic load on the ultrasonic transducer as caused by the condition of the septum.

During operation in impedance mode, a number of output signals may be obtained at different applied frequencies as desired to obtain an accurate indication of the acoustic load on the ultrasonic transducer. Alternatively, a number of data points may be obtained by the controller at different applied frequencies, with the different data points being correlated to a condition of the septum. That condition indication may then be used to generate a single output signal indicative of the condition of the septum at time $t_0$.

The needle (or other fluid delivery device) is then advanced 84 towards the reservoir and its associated septum. The exact position of the needle relative to the implanted medical device may be determined by a variety of the location and methods and systems described in the background section above.

It is preferred that the advancement of the needle be delayed until after the output signal or signals have been generated for time $t_0$. By waiting to advance the needle until after the initial measurements have been taken, a baseline signal can be obtained to determine whether the needle pierces the septum as it is advanced.

During impedance operation, it may be desirable to cease emission of ultrasonic energy during advancement of the needle to conserve power within the implantable medical device. If so, after initial advancement of the needle is completed, a second round of ultrasonic energy emission into the septum can be performed after advancement of the needle. Alternatively, the ultrasonic transducer may emit ultrasonic energy continuously as the needle is advanced towards the reservoir of the implantable medical device.

Regardless of whether the ultrasonic transducer is operated continuously or not, the acoustic load on the ultrasonic transducer is sensed after advancement of the needle in manner similar to that described above. An output signal or signals are generated that are indicative of the acoustic load on the ultrasonic transducer at time $t_1$.

With the output signals from times $t_0$ and $t_1$, a comparison of the output signals $t_0$ and $t_1$ can be performed to determine whether the condition of the septum has changed between the two measurements based on the output signals generated at the different times. When operating in impedance mode, this comparison may involve multiple comparisons at different applied frequencies to obtain an accurate indication of the change in acoustic load at the different times.

It should be noted that this comparison, and the data storage required to complete it, may be accomplished within the implantable medical device itself or, alternatively, the comparison may be performed external to the patient based on the output signals which can be communicated by telemetry to an external control device. Regardless of the location of the controller used to perform the comparison functions (that is external or implanted), it will be preferred that the controller include at least some data storage capacity (digital or otherwise) to provide for comparison of the output signals obtained at different times.

With the comparison complete, a decision is made as to whether the compared output signals indicate piercing of the septum by the needle 88. If the compared output signals indicate that the septum condition has changed sufficiently to indicate piercing by the needle, then it may be desired that the implantable medical device transmit a signal 89 indicating successful piercing of the septum by the needle. Typically, that signal will be transmitted by a telemetry assembly associated with the implantable medical device. The telemetry assembly communicates with an external device that is capable of providing some indication to an operator by, for example, audible, visual, tactile, etc. techniques, that the septum has been successfully pierced by the needle.

Upon receipt of a signal indicating successful piercing of the septum, transfer of fluids through the needle may be commenced 90. That transfer may typically involve the delivery of a drug or drugs into the reservoir of the implantable medical device. Alternatively or in addition to delivery of fluids to the implantable medical device, the transfer may involve the removal of fluids from the reservoir of the implantable medical device through the needle.

If, however, the determination 88 as to whether the septum has been pierced based on the compared output signals is negative, that is, that the septum has not been pierced by the needle, then a signal is preferably sent to an external device that the needle has failed to pierce the septum 91. Typically, that signal will also be transmitted by a telemetry assembly associated with the implantable medical device. The telemetry assembly communicates with an external device that is capable of providing some indication to an operator by, for example, audible, visual, tactile, etc. techniques, that the septum has not been pierced by the needle.

Upon receipt of the signal indicating a failure to pierce the septum, the position of the needle is preferably adjusted 92. The adjustments may include simply advancing the needle further inward along the same line of advancement toward the implantable medical device. Alternatively, the adjustment may involve withdrawal of the needle (partially or completely). In still another alternative, the adjustment may involve changing only the direction along which the needle is advanced.

In any case, the needle is again advanced towards the implantable medical device 84 as performed previously (before the indication of a failure to pierce the septum was received). Another output signal or signals are generated 86. The new output signal or signals are then compared 87 with the original output signal obtained at time to, followed by a determination as to whether the septum has been pierced 88. If the determination is positive, that is, the septum has been pierced, then a signal can be transmitted and relayed to the operator that a successful piercing has occurred 89. If the determination is negative, that is, that a successful piercing has not occurred, then an appropriate signal is relayed 91 and the needle position can again be adjusted 92 as discussed above.

Figure 6:
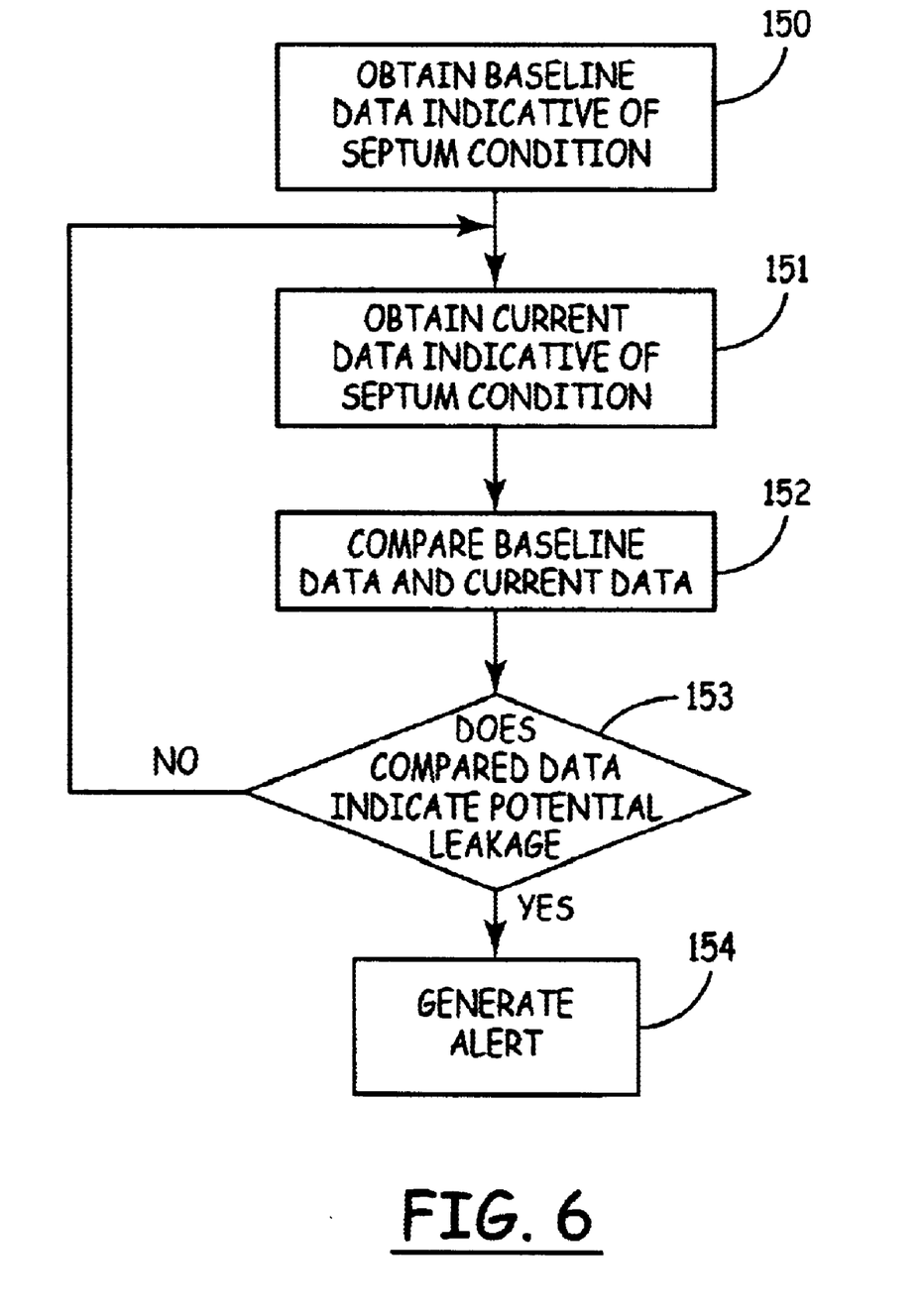
FIG. 6 is a flow chart of a method of monitoring a septum according to the present invention.

FIG. 6 illustrates another feature of the methods of the present invention, namely the ability to monitor the septum condition immediately after a needle piercing the septum has been removed or to periodically monitor the condition of the septum relative to a baseline output signal obtained earlier in the operating life of the implantable medical device.

The flowchart of FIG. 6 illustrates one embodiment of this method. The method includes obtaining baseline data indicative of the condition of the septum 150. This baseline data may, for example, be obtained by either of the methods described in connection with FIG. 4 or 5. It may preferably be based on data obtained before perforation of the septum by any needle, such that it is indicative of the original condition of the septum.

The method further involves obtaining current data indicative of the current condition of the septum 151. For example, the current data may be obtained after a needle is removed from the septum following the transfer of fluids into or out of the reservoir of an implantable medical device. Alternatively, the current data may be obtained at some selected time between fluid transfers as a part of a periodic monitoring program.

The baseline data and current data are then compared 152 to provide in indication regarding any changes in the condition of the septum. Such changes may, for example, involve inadequate resealing of the septum after removal of a needle, leakage around the perimeter of the septum, etc.

A determination is made based on the compared data to decide whether the septum is leaking 153. If the determination is positive, that is, that the septum is or may be leaking, an alert can be generated 154 to prompt further investigation of the septum condition. The alert may be visual, audible, tactile, etc. and is preferably capable of being observed by medical personnel and/or the patient in which the implantable medical device is implanted.

If the determination is negative, that is, that the condition of the septum does not indicate potential leakage, then the system returns to a point at which current data is ready to be obtained. Typically, this method will not be performed continuously to conserve power within the implantable medical device.

Figure 7:
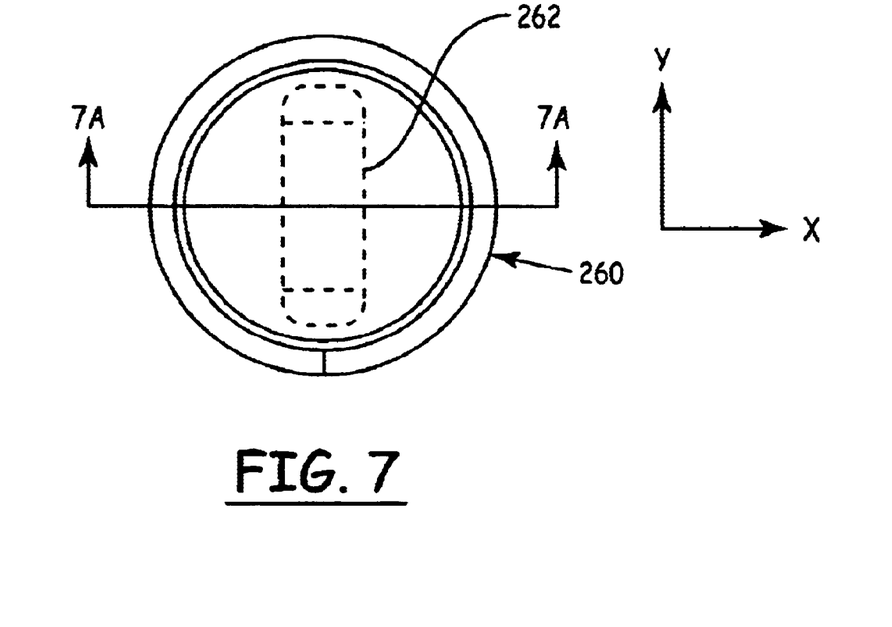
FIG. 7 is a plan view of the face of one ultrasonic transducer module for use in connection with the present invention.
Figure 7A:
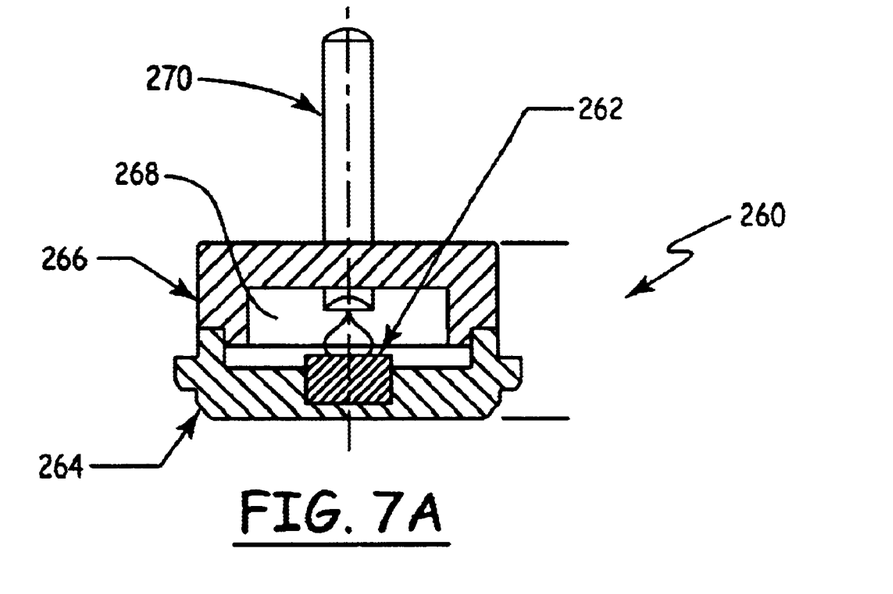
FIG. 7A is a cross-sectional view of the ultrasonic transducer module of FIG. 7, taken along line 7A—7A in FIG. 7.

FIGS. 7 and 7A depict one design for an alternative ultrasonic transducer module 260 that can be inserted into, for example, an implantable medical device such as that depicted in FIG. 2. FIG. 7A is a cross-sectional view of the module 260 taken along line 7A—7A in FIG. 7.

The module 260 includes an ultrasonic transducer 262 located within a housing 264. The ultrasonic transducer 262 is positioned within the housing 264 such that a relatively thin face of the housing is located in front of the ultrasonic transducer 262. It is that thin face of the housing 264 that is preferably in direct contact with the edge of a septum such that the transducer 262 is acoustically coupled to the septum. As such, it may be preferred that the housing 264 (or at least that face located in front of the ultrasonic transducer 262) be manufactured of material or materials that are biocompatible, resist degradation in the presence of the expected ultrasonic energy, efficiently transmit ultrasonic energy, etc. One preferred material may be, for example, titanium.

The ultrasonic transducer 262 itself will not be placed in actual physical contact with the septum because of the intervening thin face of the housing 264. For the purposes of the present invention, however, the ultrasonic transducer 262 will be considered to be directly acoustically coupled to a septum located in physical contact with the face of the housing 264.

The shape of the ultrasonic transducer 262 as seen in FIG. 7 may be beneficial in that the relatively narrow size of the active face of the transducer 262 along the x axis may result in a widely diverging acoustic energy waveform within the plane of the opening (on which the x-axis is located). In some instances, the narrow face of the transducer 262 along the x-axis may assist the transducer 262 in operating in a manner that approximates a point source of ultrasonic energy.

The dimension of the active face of the transducer 262 as measured along the y-axis is preferably equivalent to the thickness of the septum such that the ultrasonic energy is emitted through the thickness of the septum. When assembled into an implantable medical device, it may be preferred that the transducer be oriented such that the y-axis of FIG. 7 is aligned with the insertion axis 15 of FIG. 2.

The module 260 also includes a cover 266 that, together with housing 264, defines an air space 268 within the module 260. The air space 268 may improve performance of the ultrasonic transducer 262. The housing 264 and cover 266 of the module 260 may be sealed by any suitable technique, for example, welding, adhesives, etc.

FIG. 7A also depicts a lead 270 used to transmit electrical energy and signals to and from the transducer 262. The depicted lead 270 includes two conductors connected to the transducer 262. If the housing 264 is itself electrically conductive, the transducer 262 should be electrically isolated from the housing 264 by, for example, a nonconductive adhesive or other techniques. Any technique used to electrically isolate the transducer 262 from the housing 264 should not, however, interfere with the acoustic coupling between the transducer 262 and the housing 264 (with subsequent direct acoustic coupling with a septum in the implantable medical device).

In an alternative to the two-conductor lead 270 as depicted in FIG. 7A, it should be understood that a single conductor lead may be substituted if the transducer 262 is in electrical communication with an electrically conductive housing 264 that is held at a common ground with the remainder of the implantable medical device. In this configuration, the system electronics that deliver to and/or receive signals from the transducer 262 will typically need to be adaptable to the changing level of the common ground that may be experienced in an implantable medical device The methods described in connection with FIGS. 4 & 5 above may involve signal subtraction when comparing the signals obtained at different times to determine, for example, the presence or absence of a needle in the septum, leakage through the septum, etc. When used in connection with pulse mode operation, subtraction methods may preferably be performed during multiple discrete selected time intervals. Those time intervals can be selected to account for the time required for the reflected acoustic energy to travel through the septum. For example, a needle inserted into the septum close to the transducer will result in an early reflection of energy, while the acoustic energy reflected from a needle inserted into the septum at a location more distant from the transducer can be expected to return at a later time. Although accurate, signal subtraction methods may require data acquisition, digitization, and storage to an extent that is not feasible within the limited power budget available in an implantable medical device.

Figure 8:
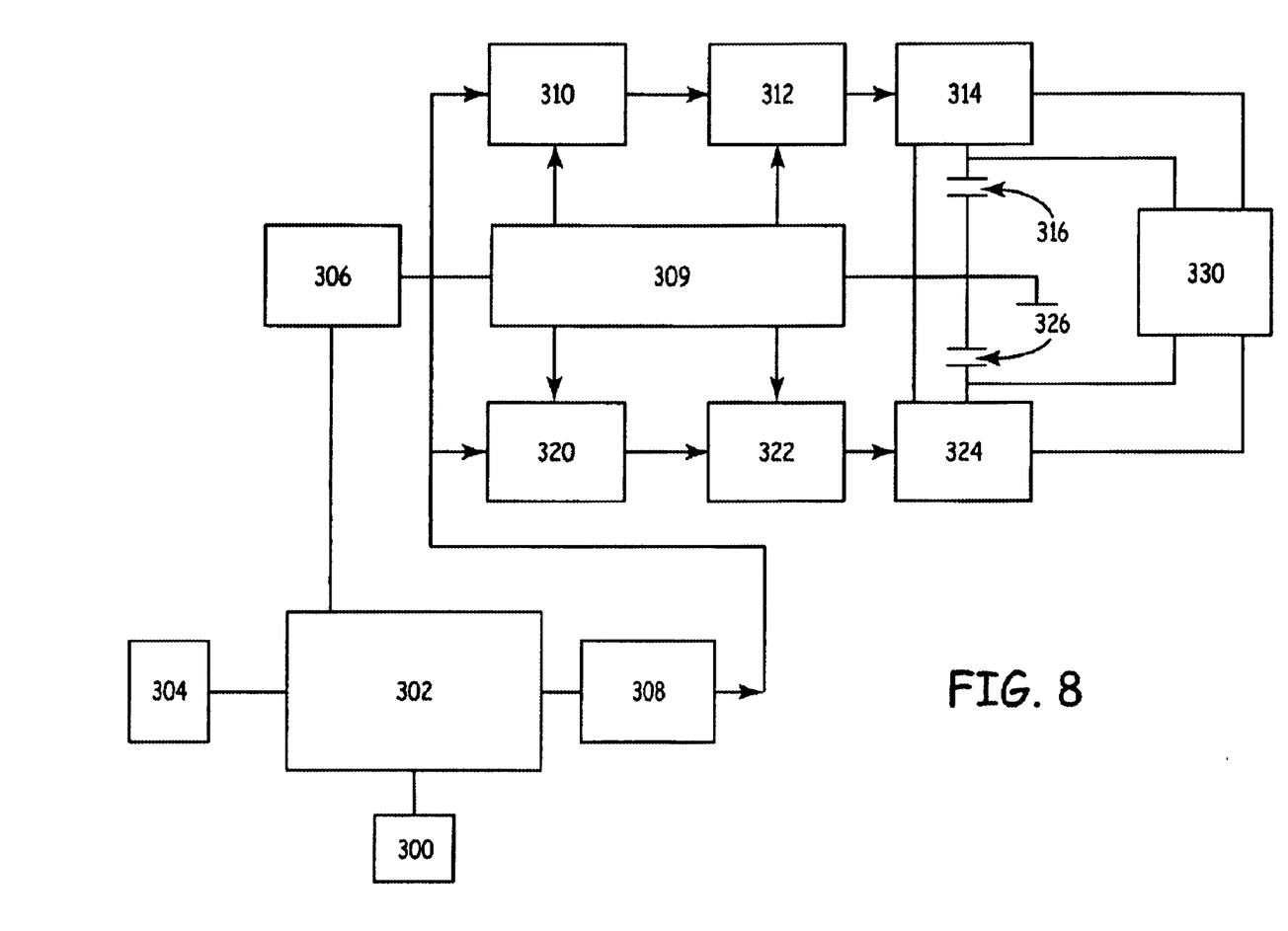
FIG. 8 is a schematic diagram of one ultrasonic transducer actuation and signal processing system/method for use in connection with the present invention.

FIG. 8 is a schematic diagram of one ultrasonic transducer actuation and signal processing system and method according to the present invention that may be useful in place of a system and method relying on baseline signal subtraction. The system of FIG. 8 is, perhaps, best suited for use in pulse mode as discussed above. Although specific time intervals, power levels, etc. are discussed below, it should be understood that such variables may change based on factors such as septum size, transducer characteristics, etc.

The system includes an ultrasonic transducer 300 connected to a transceiver 302. The ultrasonic transducer 300 may operate as an emitter (emitting ultrasonic energy) or as a sensor (sensing ultrasonic energy). The transceiver 302 may preferably include, for example, analog components such as a pulse amplifier, ultrasonic transducer amplifier (for signals received from the ultrasonic transducer 300 when operating as a sensor), and switches as required for control.

The transceiver 302 is connected to a power supply 304 capable of providing the desired amount of energy for the ultrasonic transducer 300 when operating as an emitter.

Pulsing of the ultrasonic transducer 300 may be controlled by, for example, a pulse generator 306 also connected to the transceiver 302. The ultrasound transducer 300 may, for example, be actuated by a pulse of 20 to 50 nanoseconds in length with an amplitude of 30 volts. Although lower voltages (for example, 5 volts) may be used, the lower voltages can place a higher demand on receiver signal-to-noise ratio. In some instances, the power supply 304 feeding into the ultrasonic transducer 300 may be increased up to 200 volts or more.

The system may also include a full wave rectifier 308 to process signals received by the transceiver 302 from the ultrasonic transducer 300 when operating as a sensor. The received reflection signal from the ultrasonic transducer is fed into the full wave rectifier 308 and integrated separately over two time periods to address the differences in reflected ultrasonic energy received during different time intervals, for example, from 5 to 19 microseconds and from 19 to 27 microseconds using an integrator 310 or 320 and sample and hold circuit 312 or 322 sampling the value of the integrator at the end of the integration period.

The output of the upper branch (integrator 310 and sample and hold circuit 312) will be indicative for the sensor signal power between, for example, 5 microseconds and 19 microseconds. Needle insertion into a septum may produce spurious reflected signals within this time frame, which can give rise to an increase in signal power in the time frame. Ultrasonic energy reflected by a needle located in the septum will not reach the opposite side of the septum, and therefore the power in the time frame of 19 microseconds to 27 microseconds may, in some instances, be expected to decrease.

As a result, monitoring of the ultrasonic energy that is performed differently over different time periods may be beneficial in making an accurate determination of needle presence in the septum. It will be understood that the particular time periods referred to herein are only exemplary in nature and, unless otherwise indicated, are not to limit the scope of the present invention.

A store/pass circuit 314 or 324 guides the baseline signals (the signals obtained before needle insertion) from the upper or lower sample and hold circuits 312 or 322 to a storage capacitor. The signals obtained from the upper or lower sample and hold circuits 312 or 322 during needle insertion (that is, after baseline signals have been obtained) may be directed to a dual comparator 330 to compare the signals obtained during needle insertion period with the baseline signals. In those cases in which both comparators 330 detect differences above a predefined threshold, a needle presence signal may be presented to the user. Prefiltering the signals (using, for example a high pass filter at 10 kHz) may increase sensor performance. By doing so, DC levels which may be present will not affect integrator performance.

The proposed method and system of FIG. 8 may work well for a majority of the septum, although some areas of the septum may reside in a relatively weak ultrasonic field and present challenges for accurate needle detection. When using signal baseline storage and subtraction even those signals are easily detected. As noted above, however, such methods or techniques may be beyond the power budget available for needle detection. One potential solution may involve amplitude modulation detection (fc=2.5 MHz) and sampling of the signal at considerable lower sampling frequency (for example, 1 MHz, starting at 5 microseconds to 24 microseconds). The resulting signals may be stored in a capacitor array for subtraction of subsequent signals.

Another approach to addressing the sensitivity problem may include adding sampling integrators, each operating in predefined time intervals with respect to the transmitter pulse. The time intervals may correspond to expected signals obtained for needles inserted into different portions of the septum relative to the location of the ultrasonic transducer. By processing and comparing data from the different time intervals in different manners, increased needle detection accuracy may be obtained.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to determining the presence of needles within a septum. The present invention is also not limited to ultrasonic monitoring of septums in implantable medical devices per se, but may find further application in the monitoring of any seal in an implantable medical device. The present invention further includes within its scope methods of making and using the systems described hereinabove.

What is claimed is:

1. A system for monitoring an implantable medical device comprising:
    an implantable medical device that comprises:
        a reservoir defining a volume, the reservoir comprising an opening formed therein;
        a septum attached to the reservoir, the septum sealing the opening, such that the volume defined by the reservoir is enclosed by the reservoir and the septum;
        an ultrasonic transducer arranged to emit ultrasonic energy into the septum;
        a detector arranged to detect the ultrasonic energy emitted by the ultrasonic transducer after the ultrasonic energy passes through at least a portion of the septum, whereby changes in the condition of the septum can be identified based on detection of the ultrasonic energy by the detector; and
        a transmitter capable of generating output signals.

2. A system according to claim 1, wherein the ultrasonic transducer is directly acoustically coupled to the septum.

3. A system according to claim 1, wherein the detector comprises the ultrasonic transducer.

4. A system according to claim 1, further comprising a reflector positioned to reflect the ultrasonic energy to the detector after the ultrasonic energy passes through at least a portion of the septum.

5. A system according to claim 4, wherein the reflector comprises the opening sealed by the septum.

6. A system according to claim 1, wherein the opening defines an opening plane and an insertion axis normal to the opening plane, and wherein the ultrasonic transducer emits ultrasonic energy in a direction transverse to the insertion axis.

7. A system according to claim 1, wherein the ultrasonic transducer emits ultrasonic energy in a direction across the opening.

8. A system according to claim 1, wherein the detector generates a signal indicative of the ultrasonic energy detected by the detector, and wherein the system further comprises a signal processing device operatively coupled to the detector, the signal processing device capable of comparing the signal generated by the detector at different times to identify changes in the condition of the septum.

9. A system for monitoring an implantable medical device comprising:
    an implantable medical device that comprises:
        a reservoir defining a volume, the reservoir comprising an opening formed therein, the opening defining an insertion axis;
        a septum attached to the reservoir, the septum sealing the opening, such that the volume defined by the reservoir is enclosed;
        an ultrasonic transducer arranged to emit ultrasonic energy into the septum in a direction transverse to the insertion axis;
        a detector arranged to detect the ultrasonic energy emitted by the ultrasonic transducer after the ultrasonic energy passes through at least a portion of the septum, whereby changes in the condition of the septum can be determined based on detection of the ultrasonic energy by the detector; and
        a transmitter capable of generating output signals.

10. A system according to claim 9, wherein the ultrasonic transducer is directly acoustically coupled to the septum.

11. A system according to claim 9, wherein the detector comprises the ultrasonic transducer.

12. A system according to claim 9, further comprising a reflector positioned to reflect the ultrasonic energy to the detector after the ultrasonic energy passes through at least a portion of the septum.

13. A system according to claim 12, wherein the reflector comprises the opening sealed by the septum.

14. A system according to claim 9, wherein the direction transverse to the insertion axis extends across the opening.

15. A system according to claim 9, wherein the detector generates a signal indicative of the ultrasonic energy detected by the detector, and wherein the system further comprises a signal processing device operatively coupled to the detector, the signal processing device capable of comparing the signal generated by the detector at different times to identify changes in the condition of the septum.

16. A system for monitoring an implantable medical device comprising:
    an implantable medical device that comprises:
        a reservoir defining a volume, the reservoir comprising an opening formed therein;
        a septum attached to the reservoir, the septum sealing the opening, such that the volume defined by the reservoir is enclosed by the reservoir and the septum;
        an ultrasonic transducer arranged to emit ultrasonic energy into the septum;
        a load sensor operatively coupled to the ultrasonic transducer, the load sensor capable of determining the acoustic load of the ultrasonic transducer when the ultrasonic transducer is emitting ultrasonic energy, whereby changes in the condition of the septum can be identified; and
        a transmitter capable of generating output signals.

17. A system according to claim 16, wherein the ultrasonic transducer is directly acoustically coupled to the septum.

18. A system according to claim 16, wherein the opening defines an opening plane and an insertion axis normal to the opening plane, and wherein the ultrasonic transducer emits ultrasonic energy in a direction transverse to the insertion axis.

19. A system according to claim 16, wherein the ultrasonic transducer emits ultrasonic energy in a direction across the opening.

20. A system according to claim 16, wherein the load sensor generates a signal indicative of the acoustic load sensed by the load sensor, and wherein the system further comprises a signal processing device operatively coupled to the load sensor, the signal processing device capable of comparing the signal generated by the load sensor at different times.

21. A system for monitoring an implantable medical device comprising:
    an implantable medical device that comprises:
        a reservoir defining a volume, the reservoir comprising an opening formed therein, the opening defining an insertion axis;
        a septum attached to the reservoir, the septum sealing the opening, such that the volume defined by the reservoir is enclosed;
        an ultrasonic transducer arranged to emit ultrasonic energy into the septum in a direction transverse to the insertion axis;
        a load sensor operatively coupled to the ultrasonic transducer, the load sensor capable of determining the acoustic load of the ultrasonic transducer when the ultrasonic transducer is emitting ultrasonic energy, whereby changes in the condition of the septum can be identified; and
        a transmitter capable of generating output signals.

22. A system according to claim 21, wherein the ultrasonic transducer is directly acoustically coupled to the septum.

23. A system according to claim 21, wherein the direction transverse to the insertion axis extends across the opening.

24. A system according to claim 21, wherein the load sensor generates a signal indicative of the acoustic load sensed by the load sensor, and wherein the system further comprises a signal processing device operatively coupled to the load sensor, the signal processing device capable of comparing the signal generated by the load sensor at different times.

25. A method of monitoring an implantable medical device, the method comprising:
    providing an implantable medical device that comprises:
        a reservoir defining a volume, the reservoir comprising an opening formed therein;
        a septum attached to the reservoir, the septum sealing the opening, such that the volume defined by the reservoir is enclosed by the reservoir and the septum; and
        an ultrasonic transducer;
    emitting ultrasonic energy from the ultrasonic transducer into the septum;
    detecting the ultrasonic energy after the ultrasonic energy passes through at least a portion of the septum; and
    identifying a change in condition of the septum based on detecting the ultrasonic energy after the ultrasonic energy passes through at least a portion of the septum.

26. A method according to claim 25, wherein the determining a change in condition of the septum comprises:
    generating an output signal based on the detecting the ultrasonic energy after the ultrasonic energy passes through at least a portion of the septum; and
    comparing the output signal generated at a first time with the output signal generated at a second time to identify the change in condition of the septum.

27. A method according to claim 25, wherein the ultrasonic transducer is directly acoustically coupled to the septum.

28. A method according to claim 25, wherein the detecting comprises detecting the ultrasonic energy using the ultrasonic transducer.

29. A method according to claim 25, further comprising reflecting the ultrasonic energy before detecting the ultrasonic energy.

30. A method according to claim 29, wherein the reflecting comprises reflecting the ultrasonic energy within the opening sealed by the septum.

31. A method according to claim 25, wherein the opening defines an opening plane and an insertion axis normal to the opening plane, and wherein emitting ultrasonic energy comprises emitting the ultrasonic energy in a direction transverse to the insertion axis.

32. A method according to claim 25, wherein emitting ultrasonic energy comprises emitting ultrasonic energy in a direction across the opening.

33. A method according to claim 25, further comprising notifying an operator of the change in condition of the septum after comparing the output signal generated at the first time with the output signal generated at the second time.

34. A method according to claim 25, wherein the change in condition of the septum comprises a leak in the septum.

35. A method according to claim 25, further comprising advancing a needle towards the septum, wherein the change in condition of the septum comprises presence of the needle in the septum.

36. A method according to claim 35, further comprising transferring a fluid using the needle after identifying that the change in condition of the septum comprises the presence of the needle in the septum.

37. A method according to claim 25, further comprising advancing a needle towards the septum, wherein the change in condition of the septum comprises no change in condition of the septum, and wherein the method further comprises adjusting a position of the needle, followed by advancing the needle towards the septum.

38. A method of monitoring an implantable medical device comprising:
    providing an implantable medical device that comprises:
        a reservoir defining a volume, the reservoir comprising an opening formed therein;
        a septum attached to the reservoir, the septum sealing the opening, such that the volume defined by the reservoir is enclosed by the reservoir and the septum; and
        an ultrasonic transducer;
    emitting ultrasonic energy from the ultrasonic transducer into the septum;
    sensing an acoustic load on the ultrasonic transducer to obtain a sensed acoustic load at different times when the ultrasonic transducer is emitting ultrasonic energy; and
    identifying a change in condition of the septum based on the sensed acoustic load.

39. A method according to claim 38, wherein the identifying a change in condition of the septum comprises comparing the sensed acoustic loads.

40. A method according to claim 38, wherein the ultrasonic transducer is directly acoustically coupled to the septum.

41. A method according to claim 38, wherein the opening defines an opening plane and an insertion axis normal to the opening plane, and wherein emitting ultrasonic energy comprises emitting the ultrasonic energy in a direction transverse to the insertion axis.

42. A method according to claim 38, wherein emitting ultrasonic energy comprises emitting ultrasonic energy in a direction across the opening.

43. A method according to claim 38, further comprising notifying an operator of the change in condition of the septum.

44. A method according to claim 38, wherein the change in condition of the septum comprises a leak in the septum.

45. A method according to claim 38, further comprising advancing a needle towards the septum, wherein the change in condition of the septum comprises presence of the needle in the septum.

46. A method according to claim 45, further comprising transferring a fluid using the needle after identifying that the change in condition of the septum comprises the presence of the needle in the septum.

47. A method according to claim 38, further comprising advancing a needle towards the septum, wherein the change in condition of the septum comprises no change in condition of the septum, and wherein the method further comprises adjusting a position of the needle, followed by advancing the needle towards the septum.

48. A method of transferring fluid to or from a reservoir located in an implantable medical device, the method comprising:
providing an implantable medical device that comprises:
a reservoir defining a volume, the reservoir comprising an opening formed therein;
a septum attached to the reservoir, the septum sealing the opening, such that the volume defined by the reservoir is enclosed by the reservoir and the septum; and
an ultrasonic transducer;
emitting ultrasonic energy from the ultrasonic transducer into the septum at a first time;
detecting the ultrasonic energy emitted at the first time after the ultrasonic energy passes through at least a portion of the septum;
advancing a needle towards the septum;
emitting ultrasonic energy from the ultrasonic transducer into the septum at a second time;
detecting the ultrasonic energy emitted at the second time after the ultrasonic energy passes through at least a portion of the septum;
identifying a change in condition of the septum based on detecting the ultrasonic energy emitted at the first time and the second time; and
transferring fluid to or from the reservoir using the needle if the change in the condition of the septum indicates the presence of the needle in the septum.

49. A method according to claim 48, wherein the identifying a change in condition of the septum comprises:
generating a first output signal based on detecting the ultrasonic energy emitted at the first time;
generating a second output signal based on detecting the ultrasonic energy emitted at the second time; and
comparing the first output signal and the second output signal to identify the change in condition of the septum.

50. A method according to claim 48, wherein the ultrasonic transducer is directly acoustically coupled to the septum.

51. A method according to claim 48, wherein the detecting comprises detecting the ultrasonic energy using the ultrasonic transducer.

52. A method according to claim 48, further comprising reflecting the ultrasonic energy before detecting the ultrasonic energy.

53. A method according to claim 52, wherein the reflecting comprises reflecting the ultrasonic energy within the opening sealed by the septum.

54. A method according to claim 48, wherein the opening defines an opening plane and an insertion axis normal to the opening plane, and wherein emitting ultrasonic energy comprises emitting the ultrasonic energy in a direction transverse to the insertion axis.

55. A method according to claim 48, wherein emitting ultrasonic energy comprises emitting ultrasonic energy in a direction across the opening.

56. A method of transferring fluid to or from a reservoir located in an implantable medical device, the method comprising:
providing an implantable medical device that comprises:
a reservoir defining a volume, the reservoir comprising an opening formed therein;
a septum attached to the reservoir, the septum sealing the opening, such that the volume defined by the reservoir is enclosed by the reservoir and the septum; and
an ultrasonic transducer;
emitting ultrasonic energy from the ultrasonic transducer into the septum;
sensing a first acoustic load on the ultrasonic transducer while emitting ultrasonic energy from the ultrasonic transducer into the septum at a first time;
advancing a needle towards the septum;
sensing a second acoustic load on the ultrasonic transducer while emitting ultrasonic energy from the ultrasonic transducer into the septum at a second time;
identifying a change in condition of the septum based on the first acoustic load and the second acoustic load; and
transferring fluid to or from the reservoir using the needle if the change in the condition of the septum indicates the presence of the needle in the septum.

57. A method according to claim 56, wherein the identifying a change in condition of the septum comprises comparing the first acoustic load and the second acoustic load.

58. A method according to claim 56, wherein the ultrasonic transducer is directly acoustically coupled to the septum.

59. A method according to claim 56, wherein the opening defines an opening plane and an insertion axis normal to the opening plane, and wherein emitting ultrasonic energy comprises emitting the ultrasonic energy in a direction transverse to the insertion axis.

60. A method according to claim 56, wherein emitting ultrasonic energy comprises emitting ultrasonic energy in a direction across the opening.

61. A method according to claim 56, wherein emitting ultrasonic energy from the ultrasonic transducer into the septum comprises driving the ultrasonic transducer using a swept sine wave signal.

\* \* \* \* \*

UNITED STATES PATENT AND TRADEMARK OFFICE
CERTIFICATE OF CORRECTION

PATENT NO.       : 6,740,076 B2                                        Page 1 of 1
APPLICATION NO.  : 10/132320
DATED            : May 25, 2004
INVENTOR(S)      : Richard P.M. Houben It is certified that error appears in the above-identified patent and that said Letters Patent is hereby corrected as shown below:

Title page, item [75]
Please correct the spelling of the inventor by delete "Richard Hoben" and insert --Richard P.M. Houben--.

Signed and Sealed this

Nineteenth Day of December, 2006

JON W. DUDAS
*Director of the United States Patent and Trademark Office*